United States Patent [19]

Treuner et al.

[11] 4,217,348
[45] * Aug. 12, 1980

[54] CEPHALOSPORINS HAVING AN OXAZOLIDONYLOXAMIDO SUBSTITUTED ACYL SIDECHAIN

[75] Inventors: Uwe D. Treuner; Hermann Breuer, both of Regensburg, Fed. Rep. of Germany

[73] Assignee: E. R. Squibb & Sons, Inc., Princeton, N.J.

[*] Notice: The portion of the term of this patent subsequent to Oct. 2, 1996, has been disclaimed.

[21] Appl. No.: 946,479

[22] Filed: Sep. 28, 1978

[51] Int. Cl.² .................. A61K 31/545; C07D 501/34; C07D 501/36; C07D 501/46
[52] U.S. Cl. ..................................... 424/246; 544/21; 544/22; 544/25; 544/27; 544/28
[58] Field of Search ..................... 424/246; 544/21, 22, 544/25, 27, 28

[56] References Cited

U.S. PATENT DOCUMENTS

| | | | |
|---|---|---|---|
| 3,573,294 | 3/1971 | Long et al. | 544/30 |
| 3,830,808 | 8/1974 | Clark et al. | 544/28 |
| 3,935,204 | 1/1976 | Dahlen et al. | 424/246 |
| 4,010,264 | 3/1977 | Henniger | 544/28 |
| 4,096,330 | 6/1978 | Treuner et al. | 544/27 |
| 4,113,943 | 9/1978 | Treuner et al. | 544/27 |

FOREIGN PATENT DOCUMENTS 7407815 6/1974 Netherlands.

Primary Examiner—Donald G. Daus
Assistant Examiner—David E. Wheeler
Attorney, Agent, or Firm—L. S. Levinson; D. Lovercheck; S. B. Davis

[57] ABSTRACT

Cephalosporins of the formula

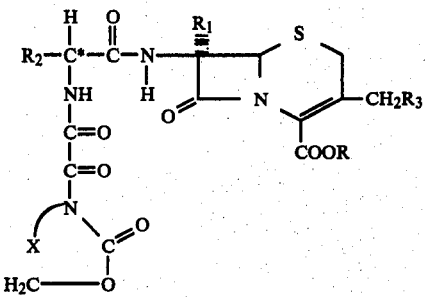

wherein R is hydrogen, sodium, potassium, or certain ester groups; $R_1$ is in the α-configuration and is hydrogen or methoxy; $R_2$ is hydrogen, lower alkyl, cycloalkyl, cycloalkenyl, cycloalkadienyl, substituted or unsubstituted phenyl, benzyl, phenethyl, thienyl, furyl, or pyridyl, or 2-amino-4-thiazolyl; X is —CH₂—, —CH₂—CH₂—,

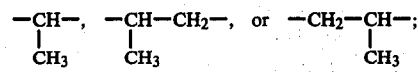

$R_3$ is hydrogen,

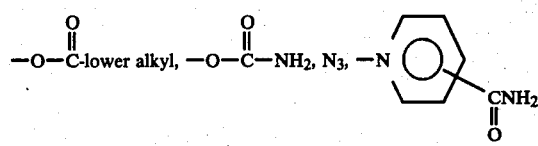

—O—lower alkyl, or certain substituted or unsubstituted heterothio groups; are disclosed. These compounds possess useful antibacterial activity.

16 Claims, No Drawings

CEPHALOSPORINS HAVING AN OXAZOLIDONYLOXAMIDO SUBSTITUTED ACYL SIDECHAIN

BACKGROUND OF THE INVENTION

Cephalosporins having various groups in the 3-position and a 7β-acyl sidechain substituted at the 2-carbon atom by a [(2-amino-1,2-dioxoethyl)amino] group are disclosed by Treuner et al. in U.S. Ser. No. 776,400 filed on Mar. 10, 1977, now U.S. Pat. No. 4,113,943.

Similarly, cephalosporins having various groups in the 3-position and a 7β-acyl sidechain substituted at the 2-carbon atom by a [(2-cyanomethylamino-1,2-dioxoethyl)amino] group are disclosed by Treuner et al. in U.S. Pat. No. 4,096,330.

Also, cephalosporins having various groups in the 3-position and a 7β-acyl sidechain substituted at the 2-carbon atom by a [(2-acylamino-1,2-dioxoethyl)amino] group are disclosed by Treuner et al. in U.S. Ser. No. 910,546 filed on May 30, 1978.

Long et al. in U.S. Pat. No. 3,573,294 disclose cephalosporins having an acetyloxymethyl group in the 3-position and a substituted or unsubstituted phenylglyoxamido group in the 7-position.

SUMMARY OF THE INVENTION

This invention is directed to cephalosporins of the formula

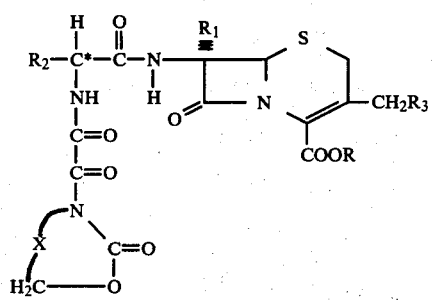

(I)

R represents hydrogen, sodium, potassium, t-butyl, benzyl, p-methoxybenzyl, p-nitrobenzyl, diphenylmethyl, 2,2,2-trichloroethyl, trimethylsilyl, —CH₂—O-lower alkyl,

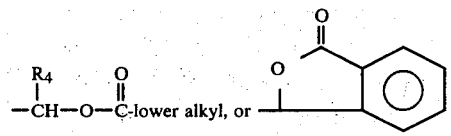

$R_1$ is in the α-configuration and is hydrogen or methoxy.

$R_2$ represents hydrogen, lower alkyl, cycloalkyl, cycloalkenyl, cycloalkadienyl,

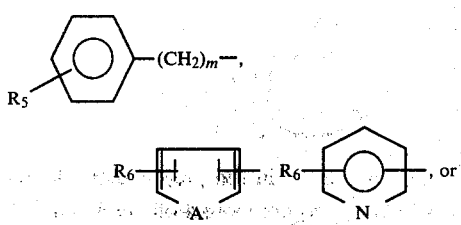

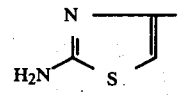

wherein $R_5$ is hydrogen, methyl, ethyl, methoxy, ethoxy, hydroxy, Cl, or Br; m is zero, 1 or 2; A is O or S; and $R_6$ is hydrogen, methyl, ethyl, Cl or Br.

$R_3$ represents hydrogen,

—O—C(=O)—lower alkyl, N₃, —O—C(=O)—NH₂, —O-lower alkyl,

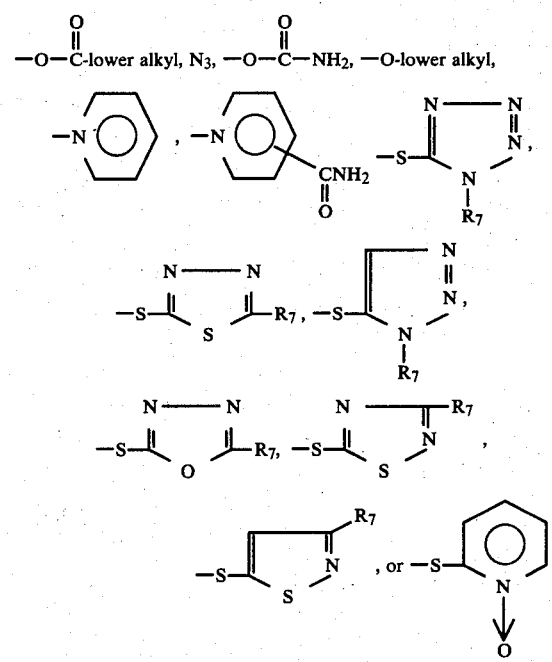

$R_7$ represents hydrogen, lower alkyl, —(CH₂)ₙ—COOR₈, —(CH₂)ₙ—SO₃R₈, or —(CH₂)ₙ—N(CH₃)₂ wherein n is an integer from 1 to 4 and $R_8$ is hydrogen, sodium, or potassium.

$R_4$ represents hydrogen or lower alkyl.

X represents —CH₂—, —CH₂—CH₂—,

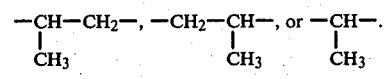

When $R_3$ is pyridinium or carbamoyl substituted pyridinium, the compounds can be structurally represented as having the formula

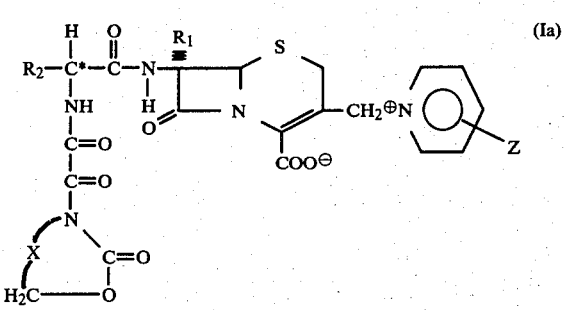

(Ia)

wherein Z is hydrogen or carbamoyl.

DETAILED DESCRIPTION OF THE INVENTION

The various groups represented by the symbols have the meaning defined below and these definitions are retained throughout this specification.

The lower alkyl groups referred to throughout this specification include straight or branched chain hydrocarbons containing 1 to 4 carbons, e.g. methyl, ethyl, i-propyl, t-butyl, etc.

Cycloalkyl refers to groups having 3 to 7 carbons in the ring, i.e. cyclopropyl, cyclobutyl, cyclopentyl, cyclohexyl, and cycloheptyl. The term cycloalkenyl represent rings having 5 to 7 carbons with one double bond, i.e. cyclopentenyl, cyclohexenyl, etc. The term cycloalkadienyl represents a ring having 6 or 7 carbons with two double bonds located at various positions such as 1,4-cyclohexadienyl which is preferred.

The compounds of formula I can be prepared by several methods. For example, when $R_3$ is hydrogen,

—O-lower alkyl,

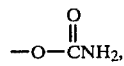

or heterothio, an α-amino compound of the formula

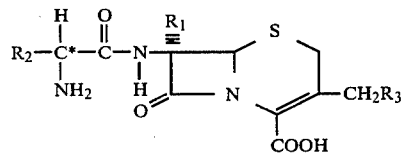

(II)

preferably in the form of its trifluoroacetic acid salt can be reacted with an acid chloride of the formula

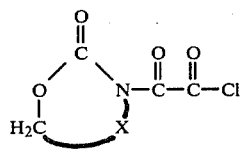

(III)

or an ester of the formula

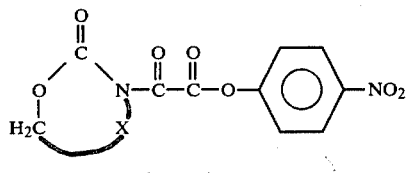

(IV)

or an ester of the formula

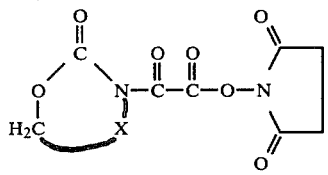

(V)

to yield the corresponding free acid compounds of formula I.

The α-amino intermediate of formula II can be prepared by various means such as by acylating a 7-amino cephalosporin of the formula

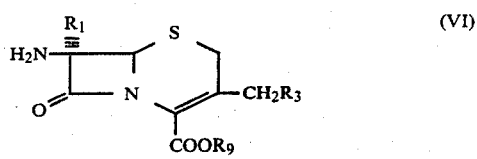

(VI)

wherein $R_9$ is a readily removable ester group such as diphenylmethyl, benzyl, substituted benzyl, t-butyl, etc.; $R_1$ is hydrogen or methoxy, and X is hydrogen,

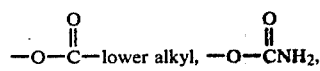

or heterothio, with a substituted α-amino acid of the formula

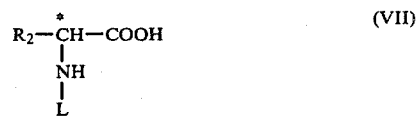

(VII)

wherein L is a protecting group such as

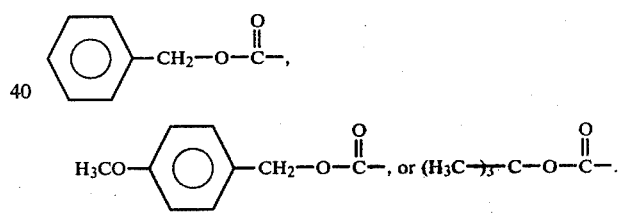

The α-amino protecting group and the ester group $R_9$ are then removed by treating the resulting cephalosporin with trifluoroacetic acid and anisole. The α-amino compounds of formula II are taught in various U.S. patents as note for example U.S. Pat. Nos. 3,641,021; 3,796,801; 3,813,388; 3,978,051; 4,061,852; 4,000,134; 3,989,697; 3,989,693; 4,088,815; 4,088,816; etc. and Belgian Pat. No. 833,640.

The acid chloride of formula III is prepared by first treating a 3-oxazolidine or 1,3-oxazine of the formula

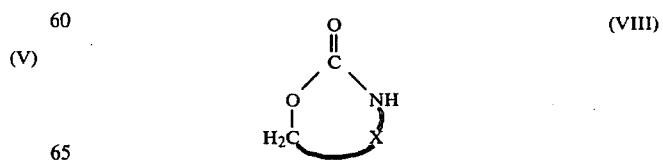

(VIII)

with trimethylsilylchloride in the presence of triethylamine to yield the silated compound of the formula

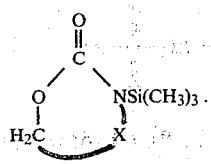

(IX)

The intermediate of formula IX is then treated with oxalyl chloride to yield the acid chloride of formula III.

The acid chloride of formula III is treated with p-nitrophenol in the presence of triethylamine to yield the ester of formula IV.

Similarly, the acid chloride of formula III is treated with N-hydroxy succinimide in the presence of triethylamine to yield the ester of formula V.

The compounds of formula I wherein $R_3$ is hydrogen

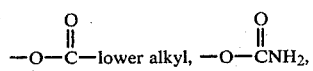

or heterothio can also be prepared by acylating a 7-amino cephalosporanic acid ester of formula VI with a compound of the formula

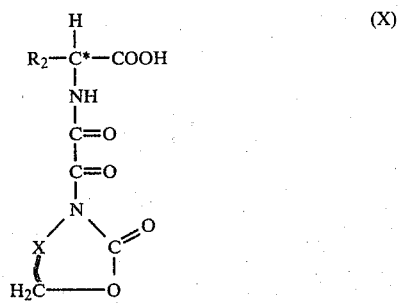

(X)

to yield the compounds of formula I in their ester form, i.e. R is t-butyl, benzyl, p-methoxybenzyl, p-nitrobenzyl, diphenylmethyl, 2,2,2-trichloroethyl, or trimethylsilyl. The ester protecting group can then be removed according to methods known in the art to yield the corresponding free acid compounds.

This acylation reaction can be performed directly with the acid of formula X by use of a coupling agent such as dicyclohexylcarbodiimide. Alternatively the acid compound of formula X can be converted to an activated derivative such as the acid chloride or bromide, an anhydride or mixed anhydride, or an activated ester formed according to methods known in the art.

The acid of formula X is prepared by reacting an α-amino acid of the formula

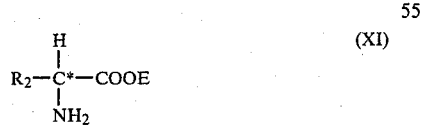

(XI)

wherein E is hydrogen or a protecting group such as diphenylmethyl or p-nitrobenzyl, with the acid chloride of formula III or the ester of formula IV or V. The protecting group can then be removed to yield the acid of formula X.

Also, when E is p-nitrobenzyl the resulting ester of formula X can be employed to directly acylate a desmethoxy 7-aminocephalosporanic acid ester of formula VI (i.e. $R_1$ is hydrogen) and yield the corresponding desmethoxy compound of formula I.

The compounds of formula Ia can be prepared by reacting a compound of formula I wherein R is hydrogen and $R_3$ is

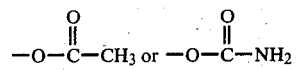

with pyridine or carbamoyl substituted pyridine in a polar solvent such as water and in the presence of a catalyst such as an alkali metal thiocyanate according to the procedures taught in U.S. Pat. No. 3,792,047 and German Offenlegungsschrift No. 2,234,280.

Similarly, the compounds of formula I wherein $R_3$ is $N_3$ are prepared by reacting a compound of formula I wherein $R_3$ is

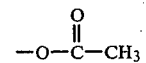

with sodium azide as taught in various U.S. patents including U.S. Pat. Nos. 3,360,515; 3,658,802; 4,006,230; etc.

Also, the compounds of formula I wherein $R_3$ is heterothio can be prepared by reacting the compound of formula I wherein R is hydrogen and $R_3$ is

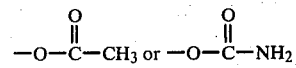

with mercaptan of the formula hetero-S-H    (XII)

or an alkali metal (preferably sodium) mercaptan salt of the formula hetero-S-alkali metal.    (XIII)

Such methods of introducing a heterothio group in the 3-position are disclosed in various U.S. patents including U.S. Pat. Nos. 3,955,213; 4,066,762; etc.

The compounds of formula I wherein R and $R_8$ are sodium or potassium are prepared by reacting the corresponding free acid of formula I (R and $R_8$ are hydrogen) with the appropriate salt forming reactant.

The compounds of formula I wherein R is

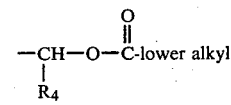

can be obtained by treating the corresponding free acid of formula I with one or two moles of a compound of the formula

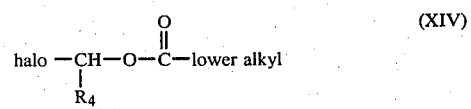

(XIV)

wherein halo is chlorine or bromine in an inert solvent such as dimethylformamide at or below ambient temperature.

Similarly, the compounds of formula I wherein R is

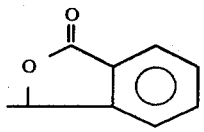

are prepared by treating the free acid compound of formula I with a compound of the formula

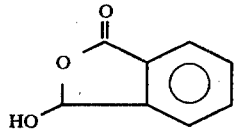 (XV)

as taught by Ferres et al. in U.S. Pat. No. 3,860,579.

The compounds of formula I wherein $R_2$ is other than hydrogen are optically active due to the presence of an asymmetric carbon atom represented as C* in the preceding formulas. By selection of the appropriate starting material it is possible to obtain the compounds of formula I as a mixture of optically active isomers or isolated as a single isomer. The various optical isomers as well as their mixtures are within the scope of this invention.

Also, the compounds of formula I and the various intermediates wherein $R_2$ is 2-amino-4-thiazolyl are tautomeric and can be structurally represented as

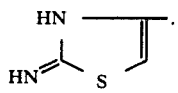

Though the 2-amino-4-thiazolyl form is being used throughout this application, both forms are within the scope of this invention.

Preferred compounds of this invention are those of formula I wherein R is hydrogen, sodium or potassium; $R_1$ is hydrogen; $R_2$ is phenyl, 2-thienyl, 3-thienyl, 2-furyl, 3-furyl, or 2-amino-4-thiazolyl; $R_3$ is hydrogen,

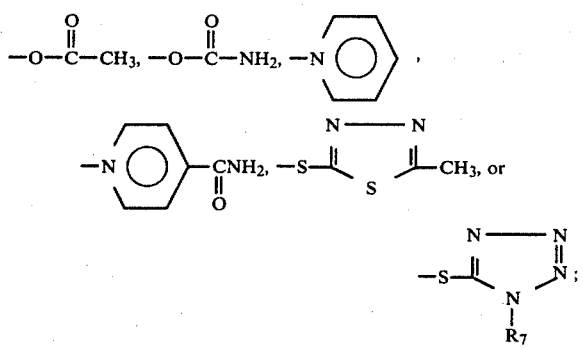

$R_7$ is hydrogen, methyl, $-CH_2-COOR_8$,

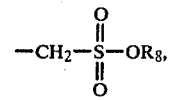

or $-(CH_2)_2-N(CH_3)_2$; $R_8$ is hydrogen, sodium or potassium; and X is $-CH_2-$.

The compounds of formula I wherein R is hydrogen, sodium, potassium, $-CH_2-O$-lower alkyl,

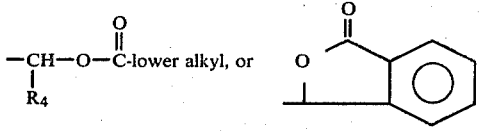

are useful antibacterial agents possessing activity against various gram-positive and gram-negative organisms such as Staphylococcus aureus, Escherichia coli, Enterobacter cloacae, Klebsiella pneumoniae, Klebsiella aerogenes, Proteus rettgeri, Proteus vulgarius, Proteus mirabilis, Serratia marcescens, Salmonella typhosa, Shigella sonnei, Citrobacter freundii, Pseudomonas aeruginosa, etc. They may be used as antibacterial agents to combat infections due to organisms such as those named above, and in general may be utilized in a manner similar to cephalothin and other cephalosporins. For example, a compound of formula I or a physiologically acceptable salt thereof may be used in various animal species in an amount of about 1 to 100 mg./kg., daily in oral or parenteral form, in single or two to four divided doses to treat infections of bacterial origin, e.g., 5.0 mg./kg. in mice.

Up to about 600 mg. of an acid compound of formula I or a physiologically acceptable salt thereof may be incorporated in an oral dosage form such as tablets, capsules or elixirs or in an injectable form in a sterile aqueous vehicle prepared according to conventional pharmaceutical practice.

Illustrative process details are provided in the examples for the various reactions. All temperatures are on the centigrade scale.

EXAMPLE 1

3-[[(1-Methyl-1H-tetrazol-5-yl)thio]methyl]-8-oxo-7β-[[D-[[oxo(2-oxo-3-oxazolidinyl)acetyl]amino]-2-thienylacetyl]amino]-5-thia-1-azabicyclo[4.2.0]oct-2-ene-2-carboxylic acid (a) α,2-Dioxo-3-oxazolidineacetyl chloride 15.92 g. of N-trimethylsilyl-2-dioxo-3-oxazolidine are dissolved in 100 ml. of methylene chloride. This mixture is slowly added dropwise at −5° to a solution of 14 g. of oxalyl chloride (10% excess). The reaction mixture is stirred for three hours and the solvent is distilled off to yield as a white solid mass α,2-dioxo-3-oxazolidineacetyl chloride; m.p. 57°.

(b)

3-[[(1-Methyl-1H-tetrazol-5-yl)thio]methyl]-8-oxo-7β-[[D-[[oxo(2-oxo-3-oxazolidinyl)acetyl]amino]-2-thienylacetyl]amino]-5-thia-1-azabicyclo[4.2.0]oct-2-ene-2-carboxylic acid 2.86 g. of 7β-[D-2-amino-2-(2-thienyl)acetamido]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt are suspended in 50 ml. of absolute acetonitrile. 3 g. of bistrimethylsilyl acetamide are added and the mixture is stirred until a clear solution is obtained. The solution is cooled to 0° and 0.6 g. of dimethylaniline are added followed by the dropwise addition of 1 g. of α,2-dioxo-3-oxazolidineacetyl chloride dissolved in 10 ml. of methylene chloride. This reaction mixture is then stirred for one hour, 15 ml. of methanol are added, and the solution is stirred for another thirty minutes. The reaction solution is then concentrated to 20 ml., stirred with 200 ml. of water and 200 ml. of ethyl acetate, and then brought to pH 2.5 by the addition of 2 N phosphoric acid. The ethyl acetate phase is washed with water and dried (Na$_2$SO$_4$). Upon concentrating, the desired product crystallizes partially and the remainder is precipitated with ether to yield as a beige powder 3-[[(1-methyl-1H-tetrazol-5-yl)thio]methyl]-8-oxo-7β-[[D-[[oxo(2-oxo-3-oxazolidinyl)acetyl]amino]-2-thienylacetyl]amino]-5-thia-1-azabicyclo[4.2.0]oct-2-ene-2-carboxylic acid; m.p. 143° (dec.).

EXAMPLE 2

3-[[(1-Methyl-1H-tetrazol-5-yl)thio]methyl]-8-oxo-7β-[[D-[[oxo(2-oxo-3-oxazolidinyl)acetyl]amino]-2-thienylacetyl]amino]-5-thia-1-azabicyclo[4.2.0]oct-2-ene-2-carboxylic acid, sodium salt The acid product of Example 1 is dissolved in a small amount of tetrahydrofuran and an equivalent proportion of sodium-2-ethyl hexanoate is added. Precipitating with diisopropyl ether yields as a beige powder 3-[[(1-methyl-1H-tetrazol-5-yl)thio]methyl]-8-oxo-7β-[[D-[[oxo(2-oxo-3-oxazolidinyl)acetyl]amino]-2-thienylacetyl]amino]-5-thia-1-azabicyclo[4.2.0]oct-2-ene-2-carboxylic acid, sodium salt; m.p. 168°.

In a similar manner, by employing potassium ethyl hexanoate one can obtain the corresponding potassium salt.

EXAMPLE 3

3-[[(1-Methyl-1H-tetrazol-5-yl)thio]methyl]-8-oxo-7β-[[D,L-[[oxo(2-oxo-3-oxazolidinyl)acetyl]amino]-2-furylacetyl]amino]-5-thia-1-azabicyclo[4.2.0]oct-2-ene-2-carboxylic acid 2.88 g. of 7β-[D,L-2-amino-2-(2-furyl)acetamido]-3-[[(1-methyl-1H-tetrazol-5-yl)thio]methyl]-8-oxo-5-thia-1-azabicyclo-[4.2.0]oct-2-ene-2-carboxylic acid, trifluoroacetic acid salt are suspended in 50 ml. of absolute acetonitrile and brought into solution by the addition of 3 g. of bistrimethylsilyl acetamide. This solution is cooled to 0° and 3 g. of propylene oxide are added followed by the dropwise addition of 1.5 g. of α,2-dioxo-3-oxazolidineacetyl chloride in 10 ml. of methylene chloride. After three hours, the product is worked up as in Example 1(b) to yield as a yellow powder 3-[[(1-methyl-1H-tetrazol-5-yl)thio]methyl]-8-oxo-7β-[[D,L-[[oxo(2-oxo-3-oxazolidinyl)acetyl]amino]-2-furylacetyl]amino]-5-thia-1-azabicyclo[4.2.0]oct-2-ene-2-carboxylic acid; m.p. 139° (dec.).

EXAMPLE 4

3-[[(1-Methyl-1H-tetrazol-5-yl)thio]methyl]-8-oxo-7β-[[D,L-[[oxo(2-oxo-3-oxazolidinyl)acetyl]amino]-2-furylacetyl]amino]-5-thia-1-azabicyclo[4.2.0]oct-2-ene-2-carboxylic acid, sodium salt The acid product of Example 3 is treated with sodium 2-ethyl hexanoate according to the procedure of Example 2 to yield 3-[[(1-methyl-1H-tetrazol-5-yl)thio]methyl]-8-oxo-7β-[[D,L-[[oxo(2-oxo-3-oxazolidinyl) acetyl]amino]-2-furylacetyl]amino]-5-thia-1-azabicyclo[4.2.0]oct-2-ene-2-carboxylic acid, sodium salt; m.p. 164°.

In a similar manner, by employing potassium ethyl hexanoate one can obtain the corresponding potassium salt.

EXAMPLE 5

3-[(Acetyloxy)methyl]-8-oxo-7β-[[D-[[oxo(2-oxo-3-oxazolidinyl)acetyl]amino]-2-thienylacetyl]amino]-5-thia-1-azabicyclo[4.2.0]oct-2-ene-2-carboxylic acid, sodium salt Following the procedure of Example 3 but employing 3-[(acetyloxy)methyl]-7β-[D-2-amino-2(2-thienyl)acetamido]-8-oxo-5-thia-1-azabicyclo[4.2.0]oct-2-ene-2-carboxylic acid, trifluoroacetic acid salt, one obtains 3-[(acetyloxy)methyl]-8-oxo-7β-[[D-[[oxo(2-oxo-3-oxazolidinyl)acetyl]amino]-2-thienylacetyl]amino]-5-thia-1-azabicyclo[4.2.0]oct-2-ene-2-carboxylic acid.

Treatment of the above acid product with sodium 2-ethyl hexanoate according to the procedure of Example 2 yields 3-[(acetyloxy)methyl]-8-oxo-7β-[[D-[[oxo(2-oxo-3-oxazolidinyl)acetyl]amino]-2-thienylacetyl]amino]-5-thia-1-azabicyclo[4.2.0]oct-2-ene-2-carboxylic acid, sodium salt.

In an analogous manner, one can obtain the corresponding potassium salt product.

EXAMPLES 6–40

Following the procedure of Example 1 but employing the acid chloride shown in Col. I and the trifluoroacetic acid salt shown in Col. II, one obtains the product shown in Col. III.

| Ex. | X | R₃ | R₁ | R₂ |
|---|---|---|---|---|
| 6 | $-CH_2-$ | 1-methyl-tetrazol-5-yl-thio | $-H$ | phenyl |
| 7 | $-CH_2-$ | 1-methyl-tetrazol-5-yl-thio | $-H$ | 2-aminothiazol-4-yl |
| 8 | $-CH_2-$ | (4-methyl-1,3,4-thiadiazol-2-yl)thio | $-H$ | thien-2-yl |
| 9 | $-CH_2-$ | 1-methyl-tetrazol-5-yl-thio | $-OCH_3$ | thien-2-yl |
| 10 | $-CH_2-CH_2-$ | 1-methyl-tetrazol-5-yl-thio | $-H$ | thien-2-yl |
| 11 | $-CH_2-CH_2-$ | 1-methyl-tetrazol-5-yl-thio | $-H$ | thien-2-yl |
| 12 | $-CH_2-CH_2-$ | 1-methyl-tetrazol-5-yl-thio | $-OCH_3$ | phenyl |
| 13 | $-CH(CH_3)-$ | 1-methyl-tetrazol-5-yl-thio | $-H$ | 2-aminothiazol-4-yl |

-continued

| | Col. I | Col. II |
|---|---|---|

| | Col. III | |
|---|---|---|

| Ex. | X | R$_3$ | R$_1$ | R$_2$ |
|---|---|---|---|---|
| 14 | —CH—<br>\|<br>CH$_3$ | tetrazole-S- with N-CH$_3$ | —H | 2-chlorothienyl |
| 15 | —CH—CH$_2$—<br>\|<br>CH$_3$ | thiadiazole-S- with CH$_3$ | —H | 3-methylfuryl |
| 16 | —CH—CH$_2$—<br>\|<br>CH$_3$ | tetrazole-S- with N-CH$_3$ | —H | 4-hydroxyphenyl |
| 17 | —CH$_2$—CH—<br>\|<br>CH$_3$ | tetrazole-S- with N-CH$_3$ | —OCH$_3$ | thienyl |
| 18 | —CH—CH$_2$—<br>\|<br>CH$_3$ | tetrazole-S- with N-H | —H | phenyl-(CH$_2$)$_2$— |
| 19 | —CH$_2$— | oxadiazole-S- with CH$_3$ | —H | H$_3$CO—C$_6$H$_4$—CH$_2$— |
| 20 | —CH$_2$—CH$_2$— | thiazole-S- with CH$_3$ | —H | 3-chlorophenyl |
| 21 | —CH$_2$— | thiazole-S- with CH$_3$ | —H | —C$_2$H$_5$ |
| 22 | —CH$_2$—CH$_2$— | pyridyl-S- N→O | —H | phenyl |

-continued

| | Col. I | Col. II |
|---|---|---|

[Col. I: cyclic structure with H₂C-X-N-C(=O)-C(=O)-Cl and O-C(=O)]

[Col. II: R₂-C*(H)(NH₂)-C(=O)-NH-C(R₁)-...-S ring with CH₂R₃ and COOH; HOOCCF₃]

Col. III

[Structure showing R₂-C*(H)-NH-C(=O)-N- with cephalosporin ring bearing R₁, S, CH₂R₃, COOH; and NH-C(=O)-C(=O)-N linked to cyclic H₂C-X / O-C=O]

| Ex. | X | R₃ | R₁ | R₂ |
|---|---|---|---|---|
| 23 | —CH₂— | —S-(1-ethyl-tetrazol-5-yl) | —H | cyclopentyl |
| 24 | —CH₂— | —S-(1H-tetrazol-5-yl) | —H | cyclohexenyl |
| 25 | —CH(CH₃)— | —S-(4-methyl-thiadiazol-2-yl) | —H | phenyl |
| 26 | —CH₂— | —O—C(=O)—CH₃ | —H | 2-furyl |
| 27 | —CH₂— | —O—C(CH₃)₃ | —H | phenyl |
| 28 | —CH₂— | —O—C(=O)—CH₃ | —H | 2-aminothiazol-4-yl |
| 29 | —CH₂—CH₂— | —O—C(=O)—CH₃ | —OCH₃ | 2-thienyl |
| 30 | —CH(CH₃)— | —O—C(=O)—CH₃ | —H | 2-thienyl |
| 31 | —CH₂— | —O—C(=O)—NH₂ | —H | 2-thienyl |
| 32 | —CH₂— | —O—C(=O)—NH₂ | —H | 2-furyl |
| 33 | —CH₂— | —O—C(=O)—NH₂ | —H | phenyl |

-continued

| | Col. I | Col. II | Col. III |
|---|---|---|---|

(Structures shown for Col. I: cyclic acid chloride with X, CH₂, N-C(=O)-C(=O)-Cl; Col. II: R₂-C*H(NH₂)-C(=O)-NH-C(R₁)- attached to bicyclic β-lactam with CH₂R₃ substituent and COOH, plus HOOCCF₃; Col. III: combined coupled product.)

| Ex. | X | R₃ | R₁ | R₂ |
|---|---|---|---|---|
| 34 | —CH₂— | —O—C(=O)—NH₂ | —H | 2-amino-thiazol-4-yl |
| 35 | —CH₂—CH₂— | —O—C(=O)—NH₂ | —OCH₃ | 2-thienyl |
| 36 | —CH₂—CH(CH₃)— | —O—CH₃ | —H | 2-thienyl |
| 37 | —CH₂— | —S-(1-CH₂COOH-tetrazol-5-yl) | —H | 2-thienyl |
| 38 | —CH₂— | —S-(1-CH₂SO₃H-tetrazol-5-yl) | —OCH₃ | 2-thienyl |
| 39 | —CH₂— | —S-(1-(CH₂)₂N(CH₃)₂-tetrazol-5-yl) | —H | phenyl |
| 40 | —CH₂— | —H | —H | 4-pyridyl |

The compounds of Examples 6–40 are obtained as the D-, L-, or a mixture of the D- and L- isomers depending upon the optical activity of the starting material of Col. II.

The final compounds can be converted to the corresponding sodium or potassium salt as taught in Example 2. In the case of the compounds of Examples 37 and 38, the disodium or dipotassium salt would be obtained. Also, the acid products of Examples 1,3,5, and 6 to 40 can be converted to an ester form according to known methods as set forth in the specification.

EXAMPLE 41

3-[[(1-Methyl-1H-tetrazol-5-yl)thio]methyl]-8-oxo-7β-[[D-[[oxo(2-oxo-3-oxazolidinyl)acetyl]amino]-2-thienylacetyl]amino]-5-thia-1-azabicyclo[4.2.0]oct-2-ene-2-carboxylic acid The product of Example 1 can also be prepared according to the following procedure.

(a) α,2-Dioxo-3-oxazolidineacetic acid, 4-nitrophenyl ester 3.6 g. of α,2-dioxo-3-oxazolidineacetyl chloride, from Example 1(a), dissolved in methylene chloride are added dropwise at 0° to a solution of 2.78 g. of p-nitrophenol and 2.52 g. dimethylaniline in methylene chloride. After thirty minutes, the mixture is shaken with water and dilute hydrochloric acid. The organic phase is dried, concentrated, and the precipitated product is recrystallized from toluene to yield white crystalline α,2-dioxo-3-oxazolidineacetic acid, 4-nitrophenyl ester; m.p. 159°.

(b)

D-α-[[Oxo(2-oxo-3-oxazolidinyl)acetyl]amino]-2-thiopheneacetic acid, diphenylmethyl ester 3.6 g. of the 4-nitrophenyl ester from part (a) dissolved in methylene chloride are added dropwise at 5° to a solution of 6.47 g. of D-2-thienylglycine benzhydryl ester and 2.46 of dimethylaniline in methylene chloride. After stirring for thirty minutes, the mixture is shaken with water and dilute hydrochloric acid. The organic phase is dried and the solvent is evaporated to yield as a solid foam D-α-[[oxo(2-oxo-3-oxazolidinyl)acetyl]amino]-2-thiopheneacetic acid, diphenylmethyl ester; m.p. 84°.

(c)

D-α-[[Oxo(2-oxo-3-oxazolidinyl)acetyl]amino]-2-thiopheneacetic acid

The diphenylmethyl ester from part (b) is treated with a mixture of trifluoroacetic acid and anisole (4:1) at 0°. The mixture is concentrated and the residue is taken up with sodium bicarbonate solution, acidified, and extracted with ethyl acetate. The ethyl acetate is evaporated and the product is recrystallized from water to yield as a white powder D-α-[[oxo(2-oxo-3-oxazolidinyl)acetyl]amino]-2-thiopheneacetic acid; m.p. 161°.

(d)

3-[[(1-Methyl-1H-tetrazol-5-yl)thio]methyl]-8-oxo-7β-[[oxo(2-oxo-3-oxazolidinyl)acetyl]amino]-2-thienylacetyl]amino]-5-thia-1-azabicyclo[4.2.0]oct-2-ene-2-carboxylic acid, diphenylmethyl ester 2.47 g. of 7β-amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester and 1.5 g. of the 2-thiopheneacetic acid product from part (c) are dissolved in 100 ml. of absolute tetrahydrofuran. 1.03 g. of dicyclohexylcarbodimide dissolved in 10 ml. of tetrahydrofuran are added dropwise at 0°. After stirring for two hours, the reaction mixture is filtered to remove insoluble material, treated with charcoal, and concentrated. The oily residue crystallizes upon treatment with ether/petroleum ether to yield as a beige powder 3-[[(1-methyl-1H-tetrazol-5-yl)thio]methyl]-8-oxo-7β-[[D-[[oxo(2-oxo-3-oxazolidinyl)acetyl]amino]-2-thienylacetyl]amino]-5-thia-1-azabicyclo[4.2.0]oct-2-ene-2-carboxylic acid, diphenylmethyl ester; m.p. 102° (dec.).

(e)

3-[[(1-Methyl-1H-tetrazol-5-yl)thio]methyl]-8-oxo-7β-[[D-[[oxo(2-oxo-3-oxazolidinyl)acetyl]amino]-2-thienylacetyl]amino]-5-thia-1-azabicyclo[4.2.0]oct-2-ene-2-carboxylic acid The diphenylmethyl ester product from part (d) is treated at −5° with a mixture of trifluoroacetic acid and anisole (4:1) to yield as a beige powder 3-[[(1-methyl-1H-tetrazol-5-yl)thio]methyl]-8-oxo-7β-[[D-[[oxo(2-oxo-3-oxazolidinyl)acetyl]amino]-2-thienylacetyl]amino]-5-thia-1-azabicyclo[4.2.0]oct-2-ene-2-carboxylic acid; m.p. 141°–143° (dec.).

EXAMPLES 42–53

Following the procedure of Example 41 but employing the acid shown in Col. I and the 7β-aminocephalosporanic acid ester shown in Col. II, one obtains the ester product shown in Col. III. Removal of the ester protecting group yields the free acid final product shown in Col. IV.

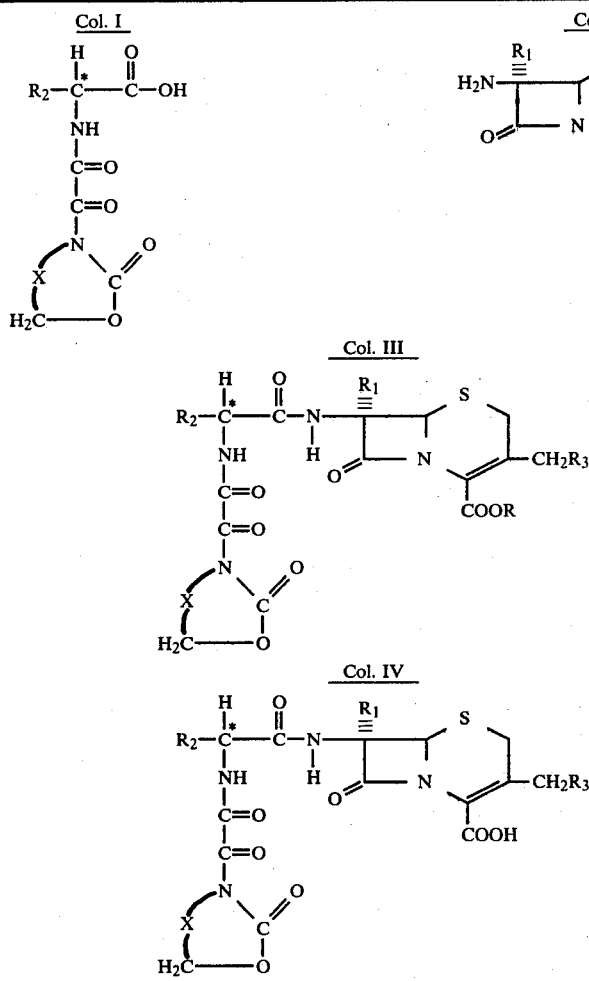
| Ex. | R₂ | X | R | R₁ | R₃ |
|---|---|---|---|---|---|
| 42 | furan-2-yl | $-CH_2-$ | $-CH(C_6H_5)_2$ | $-OCH_3$ | $-S-\text{(1-methyl-tetrazol-5-yl)}$ |
| 43 | phenyl | $-CH_2-$ | $-CH_2CCl_3$ | $-H$ | $-S-\text{(5-methyl-1,3,4-thiadiazol-2-yl)}$ |
| 44 | 2-aminothiazol-4-yl | $-CH_2-$ | $-CH_2-C_6H_4-OCH_3$ | $-H$ | $-S-\text{(5-methyl-1,3,4-oxadiazol-2-yl)}$ |
| 45 | 3-bromothien-2-yl | $-CH(CH_3)-$ | $-t-C_4H_9$ | $-H$ | $-S-\text{(1H-tetrazol-5-yl)}$ |
| 46 | 4-methylbenzyl | $-CH_2-CH_2-$ | $-CH(C_6H_5)_2$ | $-H$ | $-O-CO-CH_3$ |
| 47 | 1,4-cyclohexadien-1-yl | $-CH(CH_2)-CH_2-$ | $-CH(C_6H_5)_2$ | $-H$ | $-O-CO-NH_2$ |

-continued
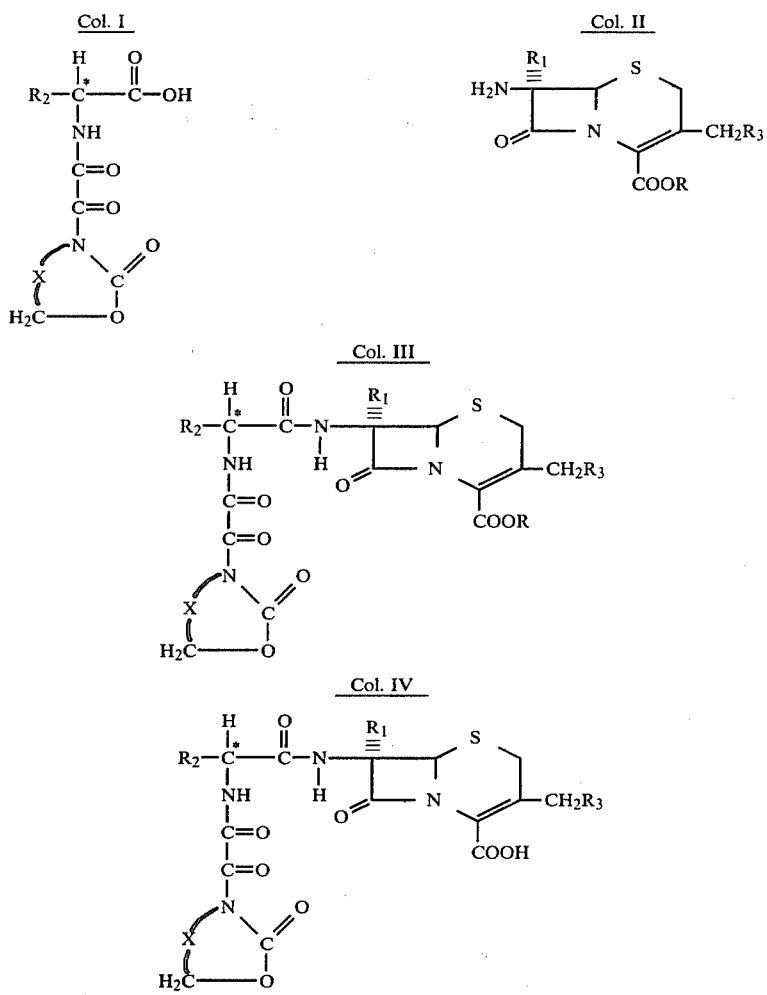
| Ex. | R₂ | X | R | R₁ | R₃ |
|-----|-----|-----|-----|-----|-----|
| 48 | furan | —CH₂—CH₂— | —CH(phenyl)₂ | —OCH₃ | -S-(1-methyl-tetrazol-5-yl) |
| 49 | furan | —CH₂—CH₂— | —CH(phenyl)₂ | —OCH₃ | -S-(1-methyl-tetrazol-5-yl) |
| 50 | 2-aminothiazol-4-yl-vinyl | —CH₂—CH(CH₃)— | —Si(CH₃)₃ | —H | —O—C(=O)—CH₃ |
| 51 | 4-hydroxyphenyl | —CH₂— | —CH(phenyl)₂ | —OCH₃ | —O—C(=O)—NH₂ |
| 52 | 3-chlorobenzyl | —CH(CH₃)— | —CH₂-(4-nitrophenyl) | —H | —O—C(=O)—C₂H₅ |

-continued

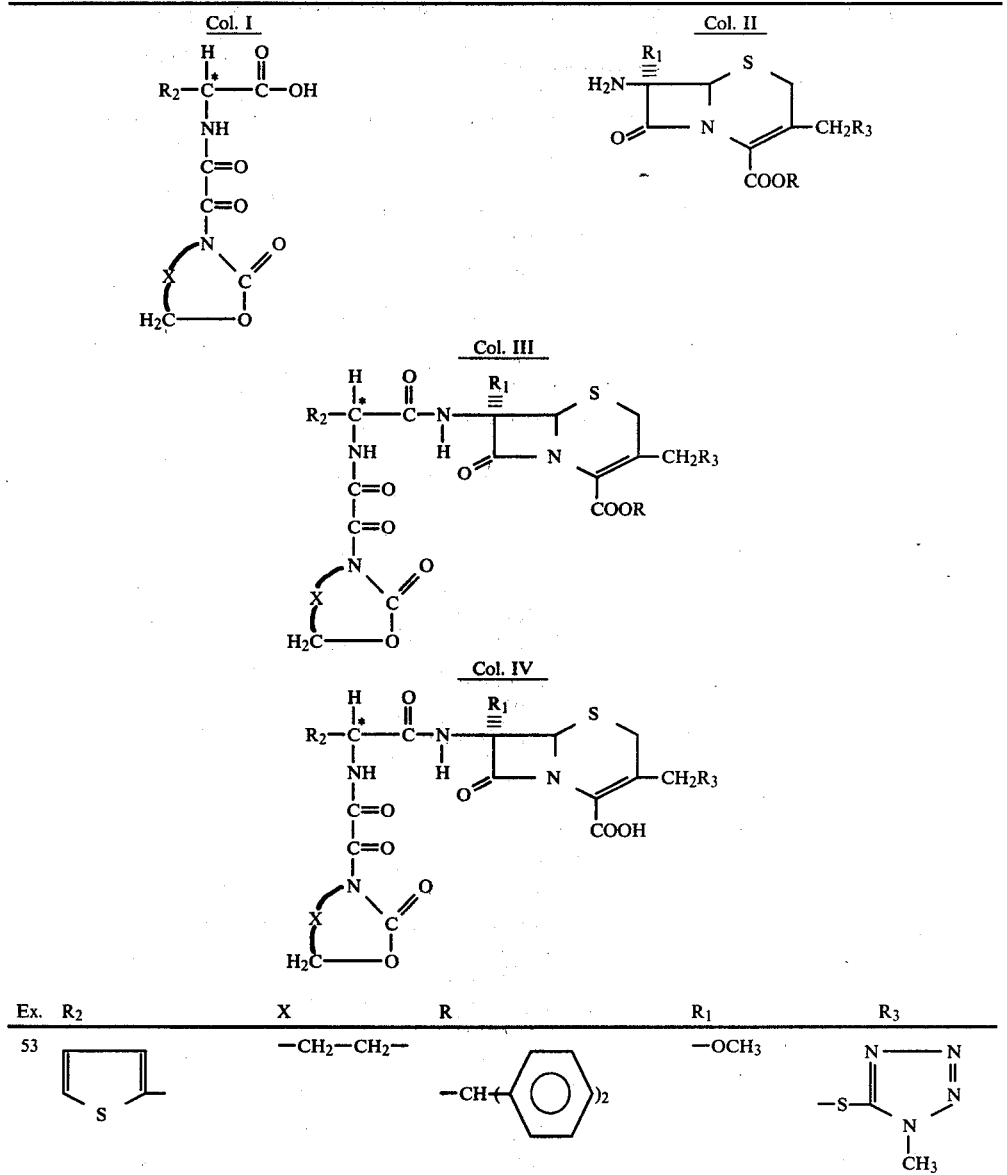

| Ex. | R₂ | X | R | R₁ | R₃ |
|---|---|---|---|---|---|
| 53 | (thienyl) | —CH₂—CH₂— | —CH(C₆H₅)₂ | —OCH₃ | (methyltetrazolylthio) |

The compounds of Examples 42–53 are obtained as the D-, L-, or a mixture of the D- and L- isomers depending upon the optical activity of the starting material of Col. I.

The final compounds can be converted to the corresponding sodium or potassium salt as taught in Example 2. Also, the acid products of Examples 42–53 can be converted to another ester form, i.e. R is

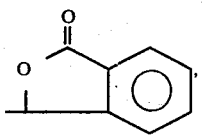

etc., according to known methods as set forth in the specification.

EXAMPLE 54

3-[[4-(Aminocarbonyl)pyridino]methyl]-7β-[[D-[[oxo(2-oxo-3-oxazolidinyl)acetyl]amino]-2-thienylacetyl]amino]-5-thia-1-azabicyclo-[4.2.0]oct-2-ene-carboxylic acid A mixture of 0.005 mole of the sodium salt product of Example 5, 0.0075 mole of 4-pyridinecarboximide, 12 g. of potassium thiocyanate, and 7.5 ml. of water are heated at 50° for 24 hours. The resulting solution is passed through a chromatography column filled with ion exchanger Amberlite XAD-2. The column is washed with water:methanol (8:2). The methanol is evaporated from the eluate and the aqueous solution is lyophilized. The amorphous residue is triturated with ether and filtered under suction to yield 3-[[4-(aminocarbonyl)pyridino]methyl]-7β-[[D-[[oxo(2-oxo-3-oxazolidinyl)acetyl]amino]-2-thienylacetyl]amino]-8-oxo-5-thia-1-azabicyclo[4.2.0]oct-2-ene-2-carboxylic acid.

EXAMPLES 55–65
Following the procedure of Example 54 but employing the cephalosporanic acid sodium salt shown in Col. I and the pyridine compound shown in Col. II, one obtains the product shown in Col. III.
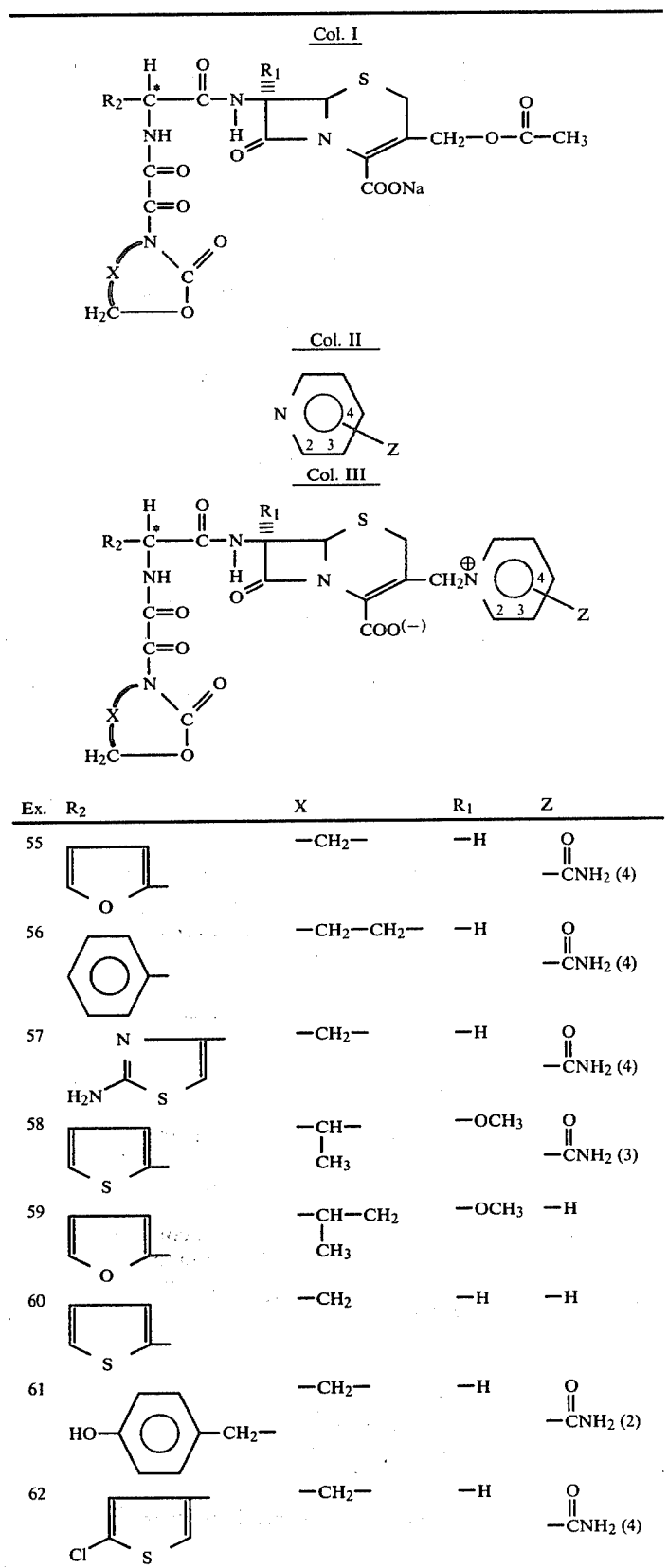

-continued

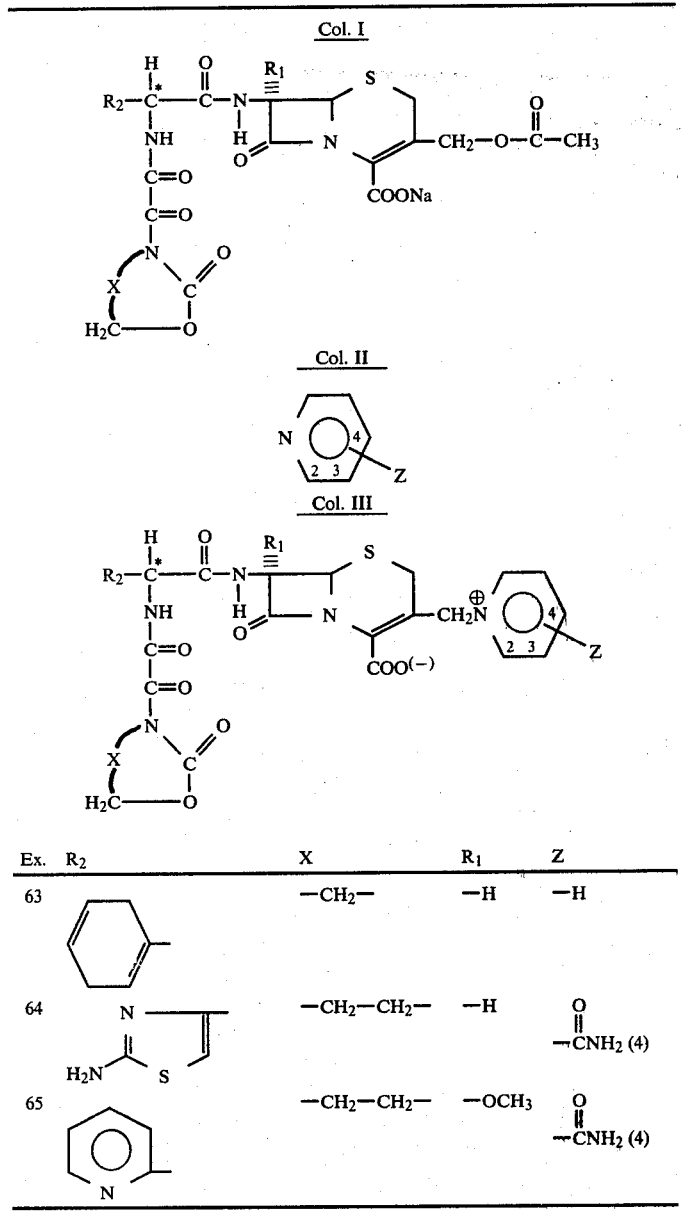

| Ex. | R₂ | X | R₁ | Z |
|---|---|---|---|---|
| 63 | ![phenyl] | —CH₂— | —H | —H |
| 64 | ![2-aminothiazolyl] | —CH₂—CH₂— | —H | $-\overset{O}{\underset{\|}{C}}NH_2$ (4) |
| 65 | ![pyridyl] | —CH₂—CH₂— | —OCH₃ | $-\overset{O}{\underset{\|}{C}}NH_2$ (4) |

The compounds of Examples 55 to 65 are obtained as the D-, L-, or a mixture of D- and L-isomers depending upon the optical activity of the starting cephalosporin shown in Col. I.

Similarly, by reacting the sodium salt of Example 5 or those shown in Col. I of Examples 52 to 65 with sodium azide according to the procedure set forth in Example 1 of U.S. Pat. No. 3,658,802, other compounds within the scope of the invention are obtained.

EXAMPLE 66

3-[[(1-Methyl-1H-tetrazol-5-yl)thio]methyl]-8-oxo-7β-[[D-[[oxo(2-oxo-3-oxazolidinyl)acetyl]amino]-2-thienylacetyl]amino]-5-thia-1-azabicyclo[4.2.0]oct-2-ene-2-carboxylic acid, sodium salt The product of Example 2 can also be prepared according to the following procedure.

0.002 mol. of the sodium salt product of Example 5 is brought into solution in 100 ml. of a phosphate buffer at a pH of 6.4. Then 0.0024 mol. of 1-methyl-1H-tetrazolyl-2-thiol is added. The solution is heated at 60° for six hours. After cooling, the pH is adjusted to 7.0 and the solution is chromatographed on the ion exchange resin Amberlite XAD-2. The fraction containing the desired product is freeze dried to yield 3-[[(1-methyl-1H-tetrao-l-5-yl)thio]methyl]-8-oxo-7β-[[D-[[oxo(2-oxo-3-oxazolidinyl)acetyl]amino]-2-thienylacetyl]amino]-5-thia-1-azabicyclo[4.2.0]oct-2-ene-2-carboxylic acid, sodium salt.

EXAMPLES 67–82

Following the procedure of Example 66 but employing the cephalosporanic acid sodium salt shown in Col. I and the thiol shown in Col. II, one obtains the product shown in Col. III.

Col. I
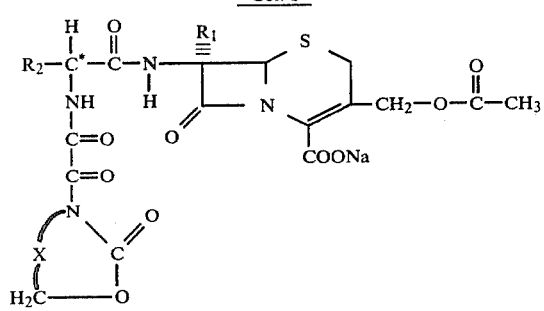
Col. II
HS-hetero
Col. III
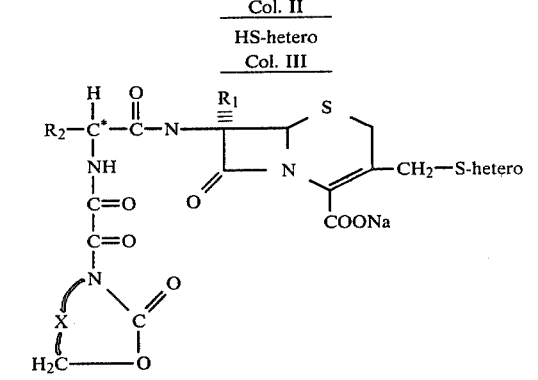
| Ex. | R$_2$ | X | R$_1$ | hetero |
|---|---|---|---|---|
| 67 | 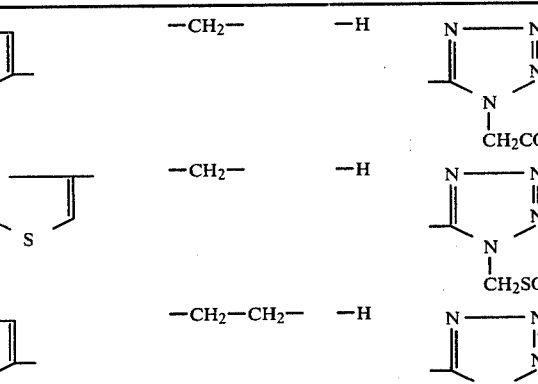 | —CH$_2$— | —H | 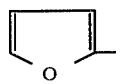 |
| 68 | 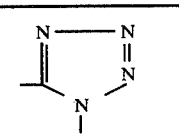 | —CH$_2$— | —H | 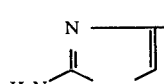 |
| 69 | 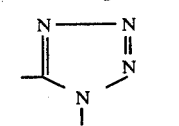 | —CH$_2$—CH$_2$— | —H | 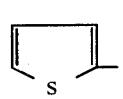 |
| 70 | 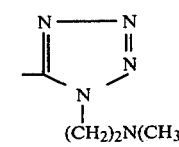 | —CH—<br>\|<br>CH$_3$ | —OCH$_3$ | 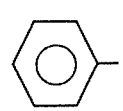 |
| 71 | 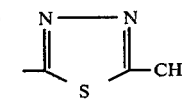 | —CH—CH$_2$—<br>\|<br>CH$_3$ | —OCH$_3$ | 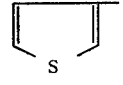 |
| 72 | 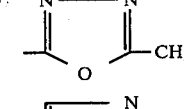 | —CH—<br>\|<br>CH$_3$ | —H | 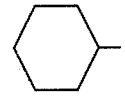 |
| 73 | 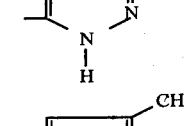 | —CH$_2$— | —H | 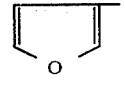 |
| 74 | 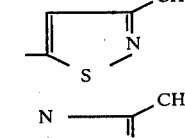 | —CH—<br>\|<br>CH$_3$ | —H | 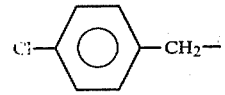 |

-continued

Col. I

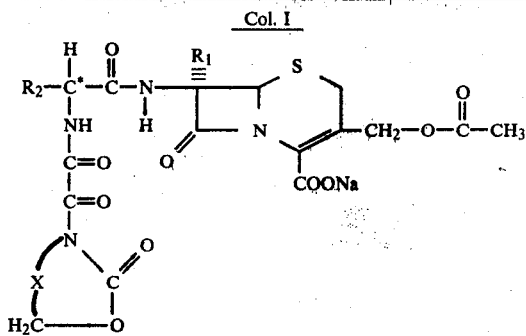

Col. II
HS-hetero
Col. III

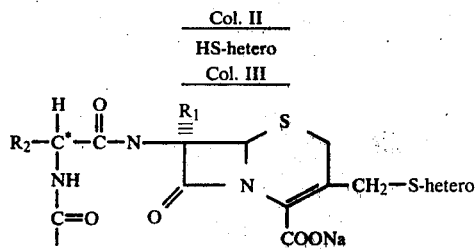

| Ex. | R₂ | X | R₁ | hetero |
|---|---|---|---|---|
| 75 | 5-Cl-thienyl | $-\underset{CH_3}{\overset{\|}{CH}}-$ | $-OCH_3$ | 1-methyl-tetrazol-5-yl |
| 76 | 2-pyridyl | $-CH_2-$ | $-H$ | 1-methyl-tetrazol-5-yl |
| 77 | 4-pyridyl | $-CH_2-CH_2-$ | $-H$ | 1-methyl-tetrazol-5-yl |
| 78 | 2-thienyl | $-CH_2-\underset{CH_3}{\overset{\|}{CH}}-$ | $-H$ | 5-(CH₂COONa)-1,3,4-thiadiazol-2-yl |
| 79 | 4-HO-phenyl | $-CH_2-$ | $-OCH_3$ | 1-methyl-tetrazol-5-yl |
| 80 | benzyl | $-\underset{CH_3}{\overset{\|}{CH}}-$ | $-H$ | 5-methyl-1,3,4-oxadiazol-2-yl |
| 81 | 2-(2-aminothiazol-4-yl)vinyl | $-\underset{CH_3}{\overset{\|}{CH}}-$ | $-H$ | pyridyl N-oxide |

-continued

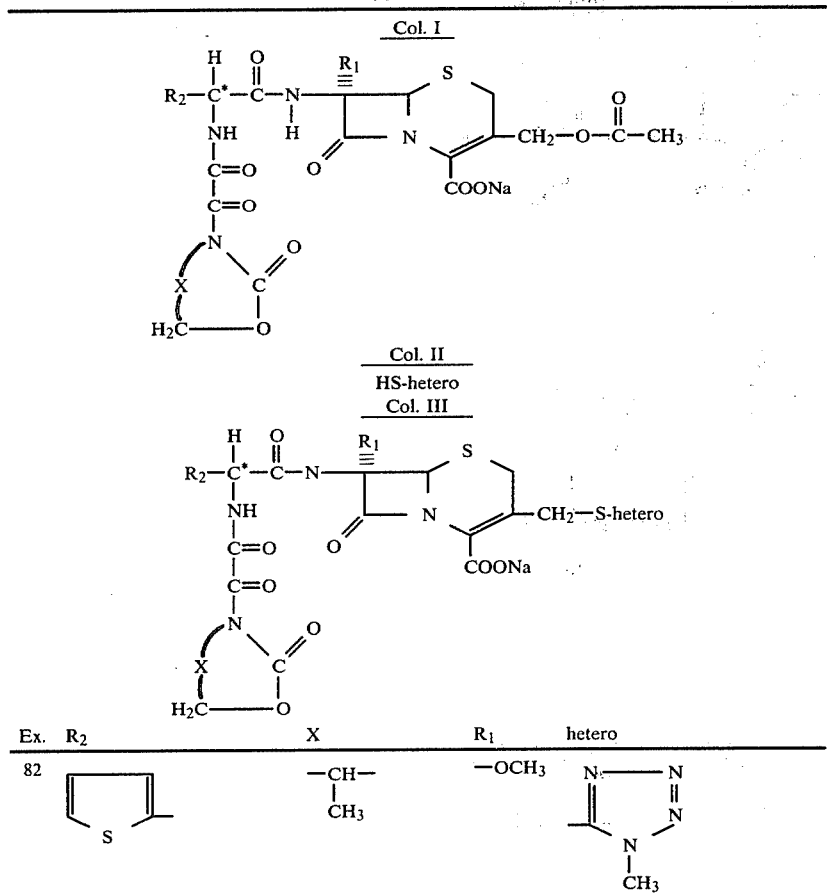

| Ex. | $R_2$ | X | $R_1$ | hetero |
|---|---|---|---|---|
| 82 | (thienyl) | $-CH(CH_3)-$ | $-OCH_3$ | (1-methyltetrazolyl) |

The compounds of Examples 67 to 82 are obtained as the D-, L-, or a mixture of D- and L- isomers depending upon the optical activity of the starting cephalosporin shown in Col. I.

What is claimed is:

1. A compound of the formula

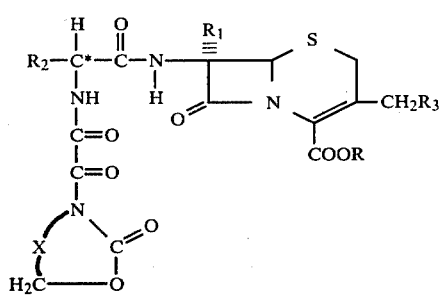

wherein R is hydrogen, sodium, potassium, t-butyl, benzyl, p-methoxybenzyl, p-nitrobenzyl, diphenylmethyl, 2,2,2-trichloroethyl, trimethylsilyl, $-CH_2-O-$ lower alkyl, $$-\underset{\underset{R_4}{|}}{CH}-O-\overset{O}{\underset{||}{C}}-\text{lower alkyl or} \quad \text{(phthalidyl)};$$

$R_1$ is in the α-configuration and is hydrogen or methoxy; $R_2$ is hydrogen, lower alkyl, cycloalkyl, cycloalkenyl, cycloalkadienyl,

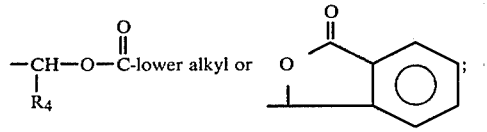

$R_4$ is hydrogen or lower alkyl; $R_5$ is hydrogen, methyl, ethyl, methoxy, ethoxy, hydroxy, Cl or Br; m is zero, 1 or 2; A is O or S; $R_6$ is hydrogen, methyl, ethyl, Cl or Br; X is $-CH_2-$, $-CH_2-CH_2-$, $$-\underset{\underset{CH_3}{|}}{CH}-, \quad -\underset{\underset{CH_3}{|}}{CH}-CH_2-, \quad \text{or} \quad -CH_2-\underset{\underset{CH_3}{|}}{CH}-;$$

$R_3$ is hydrogen, $$-O-\overset{O}{\underset{||}{C}}-\text{lower alkyl}, \quad -O-\overset{O}{\underset{||}{C}}-NH_2, \quad [N_3,]$$

$-O$-lower alkyl,

37

R<sub>7</sub> is hydrogen, lower alkyl, —(CH$_2$)$_n$—COOR$_8$, —(CH$_2$)$_n$—SO$_3$R$_8$, or —(CH$_2$)$_n$—(CH$_3$)$_2$; n is an integer from 1 to 4; and R$_8$ is hydrogen, sodium or potassium.

2. The compound of claim 1 wherein R is hydrogen, sodium, or potassium; R$_1$ is hydrogen; R$_2$ is phenyl, 2-thienyl, 3-thienyl, 2-furyl, 3-furyl, or 2-amino-4-thiazolyl; X is —CH$_2$—; R$_3$ is hydrogen, R$_7$ is hydrogen, methyl, —CH$_2$—COOR$_8$, —CH$_2$—SO$_3$R$_8$, or —(CH$_2$)$_2$N(CH$_3$)$_2$; and R$_8$ is hydrogen, sodium or potassium.

3. The compound of claim 2 wherein R$_3$ is hydrogen.
4. The compound of claim 2 wherein R$_3$ is 5. The compound of claim 2 wherein R$_3$ is 6. The compound of claim 2 wherein R$_3$ is

38

7. The compound of claim 2 wherein R$_3$ is

8. The compound of claim 7 wherein R$_2$ is 2-thienyl.
9. The compound of claim 8, 3-[[(1-methyl-1H-tetrazol-5-yl)thio]methyl]-8-oxo-7β-[[D-[[oxo(2-oxo-3-oxazolidinyl)acetyl]amino]-2-thienylacetyl]amino]-5-thia-1-azabicyclo-[4.2.0]oct-2-ene-2-carboxylic acid.
10. The sodium salt of the compound of claim 10.
11. The compound of claim 7 wherein R$_2$ is 2-furyl.
12. The compound of claim 11, 3-[[(1-methyl-1H-tetrazol-5-yl)thio]methyl]-8-oxo-7β-[[D,L-[[oxo(2-oxo-3-oxazolidinyl)acetyl]amino]-2-furylacetyl]amino]-5-thia-1-azabicyclo[4.2.0]oct-2-ene-2-carboxylic acid.
13. The sodium salt of the compound of claim 12.
14. An antibacterial pharmaceutical composition comprising a pharmaceutically acceptable carrier and one or more antibacterially active compounds of the formula:

wherein R is hydrogen, sodium, potassium, —CH$_2$—O-lower alkyl, and R$_1$, R$_2$, R$_3$, R$_4$ and X are as defined in claim 1.

15. The method of treating bacterial infections in mammals which comprises internally administering an effective amount of the composition of claim 14.
16. The compound of claim 2 having the formula wherein Z is hydrogen or carbamoyl.

* * * * *

UNITED STATES PATENT AND TRADEMARK OFFICE
CERTIFICATE OF CORRECTION

PATENT NO. : 4,217,348
DATED : August 12, 1980
INVENTOR(S) : Uwe D. Treuner, et al.

It is certified that error appears in the above-identified patent and that said Letters Patent are hereby corrected as shown below:

Col. 19, line 61, add -- [[D- -- before "[[oxo".

Col. 20, line 47, insert -- ] -- after "oxo".

Example 47 under Col. X, the formula should read:

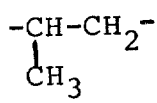

Col. 36, line 65, delete "[N$_3$]".

Signed and Sealed this

Fourth Day of November 1980

[SEAL]

Attest:

SIDNEY A. DIAMOND

Attesting Officer

Commissioner of Patents and Trademarks